United States Patent [19]

Burckhardt et al.

[11] 3,974,475
[45] Aug. 10, 1976

[54] METHOD OF AND APPARATUS FOR FOCUSING ULTRASONIC WAVES IN A FOCAL LINE

[75] Inventors: Christoph Benedikt Burckhardt, Muttenz; Pierre-André Grandchamp, Arlesheim, both of Switzerland; Heinz Hoffmann, Grenzach, Germany

[73] Assignee: Hoffmann-La Roche Inc., Nutley, N.J.

[22] Filed: Aug. 28, 1974

[21] Appl. No.: 501,313

Related U.S. Application Data

[63] Continuation of Ser. No. 294,066, Oct. 2, 1972, abandoned.

[30] Foreign Application Priority Data

Oct. 7, 1971    Switzerland.......................... 14588/71
Oct. 12, 1971   Switzerland.......................... 14848/71

[52] U.S. Cl................................... 340/15; 340/10
[51] Int. Cl.²........................................ H04B 11/00
[58] Field of Search............... 340/8 L, 8 R, 9, 10, 340/8 FT; 310/9.6; 73/67.7, 67.9; 181/165

[56] References Cited
UNITED STATES PATENTS

| | | | |
|---|---|---|---|
| 2,399,820 | 5/1946 | Morgan................................ | 340/10 |
| 2,457,393 | 12/1948 | Muffly................................ | 340/8 FT |
| 2,993,558 | 7/1961 | Reisz.................................. | 181/165 |
| 3,136,381 | 6/1964 | Anderson............................ | 340/10 |
| 3,451,260 | 6/1969 | Thurstone........................... | 73/67.9 |
| 3,599,747 | 8/1971 | Hansen............................... | 340/8 FT |
| 3,616,682 | 11/1971 | Golis et al........................... | 73/67.7 |
| 3,686,115 | 8/1972 | Farman et al....................... | 340/10 |

*Primary Examiner*—Maynard R. Wilbur
*Assistant Examiner*—T. M. Blum
*Attorney, Agent, or Firm*—Samuel L. Welt; Bernard S. Leon; Mark L. Hopkins

[57] ABSTRACT

An apparatus for focusing ultrasonic waves in a focal line by an ultrasonic optical system having at least one rotation-symmetrical, non-spherical acoustical reflection surface which together with an ultrasonic transducer element transmits an at least partially convergent ultrasonic field having an annular cross-section.

5 Claims, 3 Drawing Figures

3,974,475

METHOD OF AND APPARATUS FOR FOCUSING ULTRASONIC WAVES IN A FOCAL LINE

This is a continuation of application Ser. No. 294,066 filed Oct. 2, 1972, now abandoned.

BACKGROUND OF THE INVENTION

1. Field of the Invention

This invention relates to an apparatus for focusing ultrasonic waves in a focal line to obtain good focusing of the sound field including good lateral resolution over a considerable depth.

2. Description of the Prior Art

Ultrasonic methods are becoming increasingly important in technology and medicine, for example, in material testing or in medical diagnosis. One known method is echo sounding, in which a sound head emits an ultrasonic pulse and the pulse reflected from an obstacle is received by a different sound head or the same sound head. The distance between the transmitter/receiver and a reflecting object can be determined from the time elapsing before the echo is received.

A measure of the accuracy of an echo-sounding method is the longitudinal resolution, i.e. in the direction of the sound waves, and the lateral resolution, i.e. at right angles to the longitudinal direction. When an ordinary conventional transducer is used, a relatively good longitudinal resolution can be obtained, but the lateral resolution is inadequate because of the relatively large diameter of the ultrasonic beam. If the diameter of the sound head is reduced, the beam has a wide divergence owing to diffraction phenomena. An improvement can be obtained by weakly focusing the beam so that its diameter becomes a minimum at the center of the object under observation. The minimum diameter must not be made too small, however, since otherwise the beam divergence again becomes too large. Typically, a beam diameter of 1–2 cm is obtained if a frequency of 2 MHz is to be used for observation over a depth of 20 cm.

A much better lateral resolution can be obtained if the ultrasonic beam is focused with a wide-aperture system. The lateral resolution may be in the order of magnitude of the wavelength, i.e. about 0.75 mm in the case of 2 MHz. This good lateral resolution is obtained, however, over only a very small depth, i.e. also approximately one wavelength.

It will therefore be clear that the disadvantage of the prior-art-echo-sounding methods is due to the fact that an improvement in lateral resolution is always accompanied by a reduction of the depth over which it can be obtained.

SUMMARY OF THE INVENTION

The object of the present invention is to obtain good focusing of the sound field and hence good lateral resolution over a considerable depth. A sound field which is at least partly convergent and which has an annular cross-section is produced preferably with an ultrasonic optical system comprising at least one rotation-symmetrical, non-spherical reflection or refraction surface. Examples of rotation-symmetrical, non-spherical surfaces are conical or cylindrical surfaces or combinations thereof with spherical surfaces. Since acoustic lenses are usually highly reflecting or absorbent, it is advantageous to use reflecting surfaces, i.e. acoustic mirrors.

A sound field of this type can also be produced with an annular transmitter transducer, the receiver transducer advantageously also being annular and, if required, the transmitter transducer is also used for reception.

DESCRIPTION OF THE PREFERRED EMBODIMENT

Figure 1:
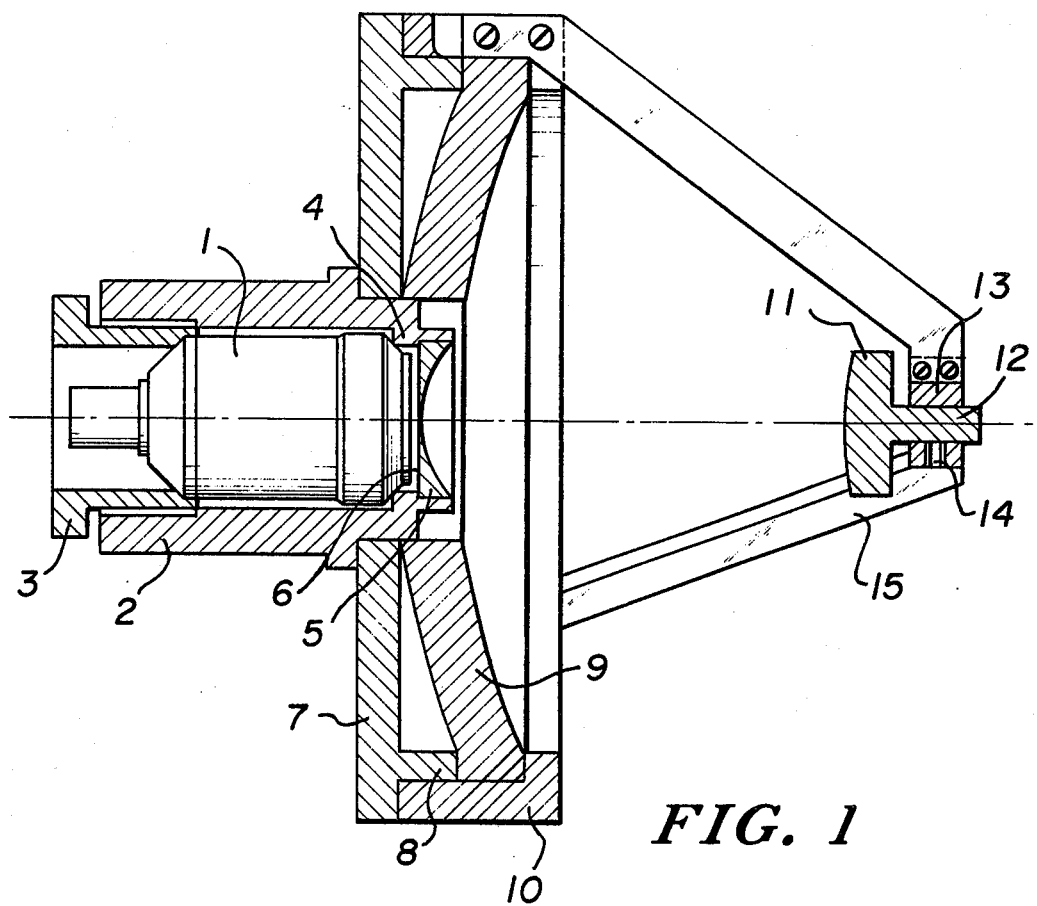
FIG. 1 shows an ultrasonic head comprising an optical system containing a non-spherical mirror.

The ultrasonic head illustrated in FIG. 1 comprises a commercially available ultrasonic transducer 1, which is disposed in a substantially cylindrical housing 2. In the present case, the diameter of the transducer comprising a piezoelectric crystal, is about 20 mm. The transducer 1 is retained by a screw cap 3 and a shoulder 4 on the inner wall of the housing, the screw cap to enable the transducer 1 to be readily removed when desired. On the side remote from the screw cap 3, the housing is closed by an ultrasonic condenser 5 consisting of a material suitable for ultrasonic lenses, in this case acrylic glass. The transducer 1 is so disposed that in its fixed position it is directly coupled to the condenser 5 by a layer 6 of an ultrasonic coupling agent, for example, silicone grease.

On the same side, the housing 2 is connected to a substantially circular support plate 7 by a screwthread provided on the outer wall of the housing.

The support plate 7 has a diameter of about 135 mm and has a continuous projection 8 at a distance of about 7 mm from its periphery. The projection 8 acts as a mounting element for an ultrasonic mirror 9, which is retained by a ring 10 connected to the support plate by screw connection. The ultrasonic mirror 9 is constructed as a concave mirror and has a non-spherical mirror surface which is symmetrical with respect to rotation about one axis. In the present case, the mirror surface has a shape formed from the combination of a conical surface and a spherical surface. The mirror 9 consists of a suitable material which reflects ultrasound, for example, brass. Another ultrasonic mirror 11 is disposed at a distance of about 75 mm from the crystal of the transducer 1 and has substantially the same diameter as the crystal and a spherical surface. It has a cylindrical rearward projection 12 by means of which it is secured in a retaining ring 13 by means of a set-screw 14. The retaining ring 13 is connected to the ring 10 by brackets 15. The mirror 11 also consists of brass, while the other fixing parts and the transducer casing are made, for example, from aluminium.

In operation, a sound pulse emitted by the transducer 1 is focussed by the condenser 5, expanded by the spherical mirror 11 and then re-focused by the mirror 9. The non-spherical shape of the mirror 9 results in a focal line instead of a focal point. The ultrasonic energy reflected by an annular zone of the mirror 9 is focused at a point of the focal line, i.e., an annular aperture of the optical system corresponds to each point of the focal line. This type of focusing in a focal line gives a narrow bunching over the entire length of this focal line and hence the possibility of good lateral resolution over a considerable depth.

ALTERNATE EMBODIMENTS

Numerous other embodiments are possible apart from the embodiment of the invention described. For example, modifications are possible by changing the path of the rays from the ultrasonic transducer to the mirror 9. Another possibility is to make the mirror 9 spherical and the mirror 11 non-spherical, or make both mirrors 11 and 9 non-spherical. The non-spherical mirror may alternatively be replaced by an acoustic lens having a non-spherical refraction surface.

Figure 2:
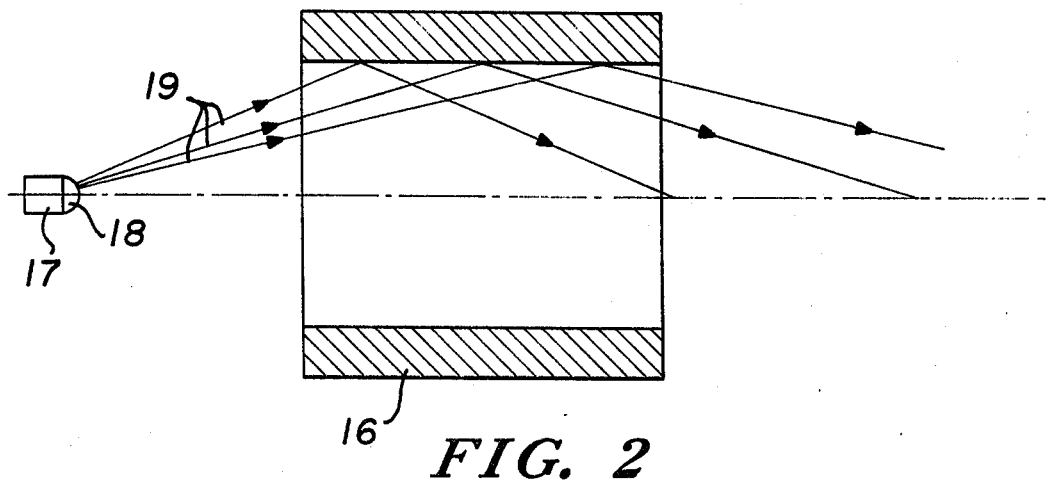
FIG. 2 shows an arrangement with a hollow cylinder as optical system diagrammatically; and, FIG. 3 is a section of an annular ultrasonic transducer having a conical radiation surface.

Apart from these modifications of the arrangement shown in FIG. 1, embodiments differing considerably from these are also possible. FIG. 2 shows a hollow cylinder 16 as an ultrasonic mirror with which it is also possible to obtain focusing in a focal line. An ultrasonic transducer 17 is disposed coaxially of the hollow cylinder 16 and advantageously has a diverging lens 18. The ultrasonic rays 19 emitted by the transducer are reflected on the inner wall of the hollow cylinder 16. All the ultrasonic rays reflected from an inner peripheral circle intersect at a point along the cylinder axis.

Figure 3:
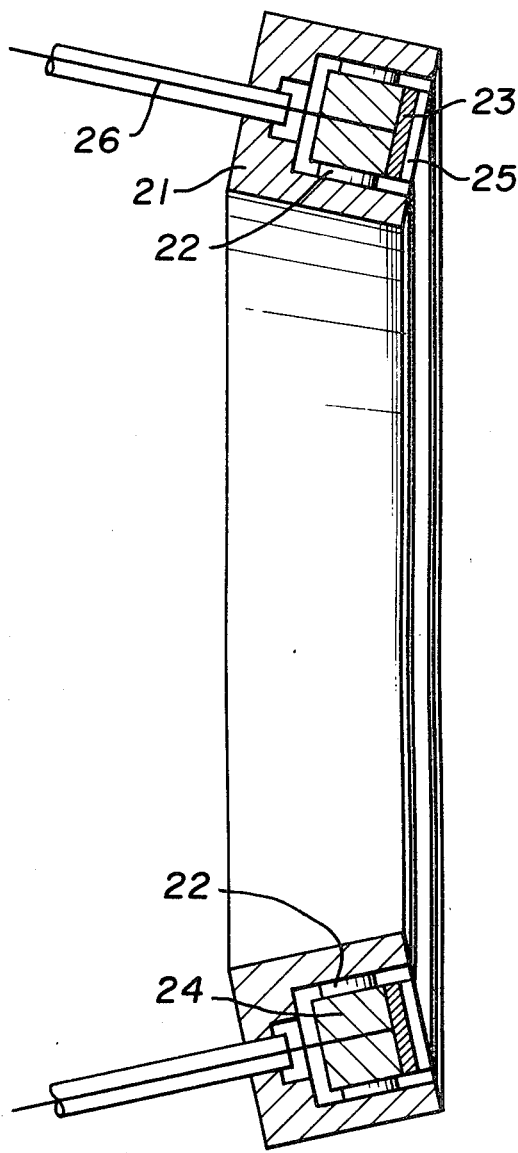

The annular transducer shown in FIG. 3 represents another possibility of producing a rotation-symmetrical and convergent sonic field. This transducer comprises an annular housing 21 of substantially U-shaped cross-section, the axis of symmetry of the cross-sectional surface being inclined to the ring axis and intersecting the same at a given distance, for example 12 cm. The open side of the U-shaped cross-section faces this point of intersection and hence the ring axis. An annular damping block 24 of epoxy resin/tungsten, which is acoustically insulated from the housing by cork panels 22, is situated in the annular recess of the housing. On the surface of the damping block 24 facing the open side of the housing there are disposed a plurality of (in this case four) flat segments 23 of a piezoelectric material, which together form a ring, and which are covered by a layer 25 of epoxy resin suitable for resistance to water. The layer 25 also provides mechanical protection for the piezoelectric oscillator formed by the segments 23. An electrical lead 26 runs to each of the segments from the back through suitable bores in the housing 21 and in the damping block 24.

The ultrasonic waves emitted by the piezoelectric oscillator form an annular bunch which focuses in a focal line on the ring axis at a certain distance from the ultrasonic transducer. The length of the focal line determines the depth over which good lateral resolution is obtained. The length of the focal line and its distance from the ultrasonic transducer must therefore be so selected that the object to be observed is illuminated over the entire depth. The distance of the focal line from the ultrasonic transducer is determined substantially by the inclination of the piezoelectric oscillator 23 to the ring axis. The length of the focal line is determined particularly by the width of the annular piezoelectric oscillator.

It is advantageous for the ultrasonic transducer unit containing the transmitter transducer to have a wide aperture of, for example more than 6°. The term "aperture" denotes the ratio of the mean ring diameter to the mean distance of the focal line from the ring. As shown in FIG. 3, the annulus diameter of the transducer unit or assembly is greater than the front-to-back cross-sectional dimensions of the assembly itself.

We claim:

1. A transducer assembly for transmitting a substantially convergent ultrasonic field focusing in a focal line, comprising an annular arrangement of ultrasonic transducers, the operating surfaces of which define a conical transmitting surface inclined towards said focal line.

2. Apparatus according to claim 1 wherein the annular transducer arrangement is composed of a plurality of sectors of an annulus.

3. Apparatus according to claim 1 wherein said transducer assembly further includes an annular base of substantially U-shaped cross-section which defines an annular recess opening in the direction of the focal line and wherein said annular transducer arrangement is composed of a plurality of transducer sectors arranged in said recess, each of which sectors has the transmitting surface thereof inclined towards the axis of said annular transducer assembly.

4. Apparatus according to claim 3 wherein said annular transducer arrangement includes ultrasonic transducer receiving means.

5. Apparatus according to claim 1 wherein the aperture of the annular transducer assembly is greater than 6°.

* * * * *